United States Patent [19]

Robin et al.

[11] Patent Number: 5,015,781

[45] Date of Patent: May 14, 1991

[54] ANESTHETIC COMPOUND AND METHOD OF PREPARING

[75] Inventors: Mark L. Robin, South Plainfield; Donald F. Halpern, Fanwood, both of N.J.

[73] Assignee: BOC, Inc., New Providence, N.J.

[21] Appl. No.: 528,944

[22] Filed: May 18, 1990

Related U.S. Application Data

[63] Continuation of Ser. No. 394,336, Aug. 15, 1989, abandoned, which is a continuation of Ser. No. 190,971, May 6, 1988, abandoned.

[51] Int. Cl.$^5$ .............................................. L07C 41/22
[52] U.S. Cl. ..................................................... 568/683
[58] Field of Search .......................................... 568/683

[56] References Cited

U.S. PATENT DOCUMENTS 3,689,459  9/1972  Regan I.
3,976,788  8/1976  Regan II.
4,762,856  8/1988  Terrell.

*Primary Examiner*—Howard T. Mars
*Attorney, Agent, or Firm*—R. Hain Swope; Larry R. Cassett

[57] ABSTRACT

The present invention is directed to a method of preparing a compound 2-(difluoromethoxy)-1,1,1,2-tetrafluoroethane by reacting 2-(difluoromethoxy)-1,1,1-trifluoro-2-chloroethane with bromine trifluoride. This reaction product is useful for inducing and maintaining anesthesia in warm blooded animals.

4 Claims, No Drawings

ANESTHETIC COMPOUND AND METHOD OF PREPARING

This is a continuation of application Ser. No. 07/394,336, filed Aug. 15, 1989, now abandoned which is a continuation of application Ser. No. 07/190,971, filed May 6, 1988, now abandoned.

FIELD OF THE INVENTION

The present invention is directed to the field of inhalation anesthetics and particularly to volatile liquid inhalation anesthetics which are used to induce and maintain anesthesia.

BACKGROUND OF THE INVENTION

Volatile liquid anesthetics are known in the art and include by way of example halothane, trichloroethylene and ether derivatives including enflurane, fluroxene, methoxyflurane, and isoflurane.

The aforementioned inhalation anesthetics overcome many of the limitations inherent in earlier agents such as chloroform and ether. These anesthetics act rapidly, have minimal or no toxicity, and are non-flammable. Despite this considerable progress, one limitation continues to be the rate at which recovery from anesthesia occurs. Although recovery is rapid, it is less rapid than might be desired, especially for patients who return home on the day of surgery (outpatient surgery).

The compound employed in the composition of the present invention, 2-(difluoromethoxy)-1,1,1,2-tetrafluoroethane or $CHF_2OCHFCF_3$, is disclosed in Example XXI of Russell et al., U.S. Pat. No. 3,897,502, which is directed to processes for making fluorinated ethers to prepare pastes and dispersions of fluorine-containing olefins, waxes to provide coatings, and degreasing agents. Furthermore, the Russell et al. patent states that some of the poly-fluoro containing products which can be made by the methods disclosed in the patent are agents for producing anesthesia in anesthetic-susceptible, air-breathing mammals.

Applicants have found that the compound of the present invention is an effective anesthetic and exhibits unexpectedly rapid induction and recovery.

It is therefore an object of the invention to provide methods of inducing and maintaining anesthesia employing an anesthetic compound that is fast acting and affords the patient rapid recovery from anesthesia.

It is a further object of the invention to provide a method of preparing said compounds in quantitative yields.

DETAILED DESCRIPTION OF THE INVENTION

The present invention is directed to an anesthesia inducing composition comprising a mixture of oxygen gas and an anesthesia inducing effective amount of a compound 2-(difluoromethoxy)-1,1,1,2-tetrafluoroethane having the formula

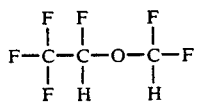

The present invention is also directed to methods of inducing and/or maintaining anesthesia by administering the composition in sufficient amounts to warm blooded animals.

The present invention is also directed to a method of preparing the compound 2-(difluoromethoxy)-1,1,1,2-tetrafluoroethane The compound of the present invention lends itself to effective use as an inhalant anesthetic in respirable mixtures containing life-supporting concentrations of oxygen, with or without other inhalation anesthetics, such as nitrous oxide Administration of the compound may be by any of the well known techniques for administering general inhalation anesthetics, for example, by using the open drop or semi-closed systems.

The effective amount of the compounds of this invention to be employed depends on the level of anesthesia to which the mammal is to be brought, the rate at which anesthesia is to be induced, and the length of time over which anesthesia is to be maintained. Minor volume percentages of the compound in oxygen can often be employed. The amount used should be sufficient to provide a significant anesthetic effect but not so much as to produce unacceptable deleterious side effects. For instance, about 1 to 8 volume percent of the compound may often be used. About 3 to 7 volume percent is preferred. The amount of anesthesia to be used can be regulated, starting with a small amount of the compound and gradually increasing the amount until the desired plane of anesthesia is reached. By then monitoring the physical reactions of the mammal, as is the usual procedure, the duration and plane of anesthesia can be readily controlled.

The compound 2-(difluoromethoxy)-1,1,1,2-tetrafluoroethane is normally a clear, colorless liquid with a slight non-pungent odor It has the following physical properties: boiling point 23.5° C., molecular weight 168, vapor pressure (est.) 660 mm Hg at 20° C., and specific gravity 1 44. The IR shows a prominent peak at 4903 and the $^1H$ NMR shows a triplet at 6.5 ppm (J=70 Hz) and a doublet of quartets at 5.9 ppm ($J_{gem}=56$ Hz, $J_{vic}=3$ Hz). The compound is non-flammable, and soda lime stable.

The compound $CHF_2OCHFCF_3$ can be prepared by the method described in U.S. Pat. No. 3,987,502 which is incorporated herein by reference. More specifically, a compound having the formula $CHF_2OCH_2CF_3$ is combined with freon and reacted with a mixture of 20% fluorine in argon followed by distillation.

In accordance with the present invention, the compound may also be prepared by reacting isoflurane ($CHF_2OCHClCF_3$) with a fluorine containing compound such as bromine trifluoride.

The starting material isoflurane (2-(difluoromethoxy)-1,1,1-trifluoro-2-chloroethane) for the present synthesis may be prepared by the methods disclosed in Terrell et al., U.S. Pat. No. 3,535,388, incorporated herein by reference. Isoflurane is also commercially available from Anaquest Division of BOC, Inc. (Madison, Wis.).

Bromine trifluoride has been found to react with isoflurane or $CHF_2OCHClCF_3$ at moderate temperatures to produce $CHF_2OCHFCF_3$ in near quantitative yields. A temperature range of 5° to 50° C. is suitable and about 30° C. is preferred. Addition of bromine trifluoride to isoflurane is characterized by increasing percent conversions as the molar ratio of $BrF_3$ to isoflurane is increased. Best results are obtained at a molar ratio of about 1:1. In the reverse addition procedure (addition of isoflurane to bromine trifluoride) near quantitative yields of $CHF_2OCHFCF_3$ are attained at a molar ratio of $BrF_3$ to isoflurane of about 0.3:1.

The rapid rate of reaction of bromine trifluoride with isoflurane renders its control extremely easy. For example, when isoflurane addition is interrupted, the reaction is immediately halted and there is an immediate drop in reaction temperature The ease of control, relatively simple equipment required and the high yields attainable make the process attractive as an industrial preparation. For reactions on the kilogram scale, an average 81% conversion and 95% yield are attainable.

Bromine trifluoride ($BrF_3$) is a hazardous material, exploding upon contact with water or organic materials. It can be safely handled by careful engineering design and adherence to proper operating procedures. At the present time bromine trifluoride is commercially available, from Air Products (Allentown, PA.)

To further illustrate the present invention, the following examples are provided, wherein the following definitions are employed:

$$\% \text{ conversion} = \frac{\text{moles product}}{\text{moles starting material fed}} \times 100$$

$$\% \text{ yield} = \frac{\text{moles product}}{\text{moles starting material consumed}} \times 100$$

GC = gas chromatograph
$t_r$ = retention time (minutes) from injection point

EXAMPLE 1

Isoflurane (171 g) was combined with 116 g of potassium fluoride in the absence of solvent and the resulting mixture was heated in an autoclave at 278° C. at 500 psi for 18 hours and then allowed to cool. The cooled mixture was subjected to gas chromatography which showed the presence of 68% of the compound $CHF_2OCHFCF_3$ and 30% unreacted isoflurane. Treatment of this mixture with excess bromine trifluoride at 15° C. in a glass vessel followed by washing with dilute sodium hydroxide and drying yielded 50 g of 98% pure product (30% yield).

The structure of $CF_3CHFOCF_2H$ may be confirmed by the following instrumental data:

$^1$H NMR doublet of quartets at $\delta = 5.9$ ppm,
  $J_{OCHF} = 54.3$ Hz
  $J_{CHF\text{-}CF_3} = 2.8$ Hz
triplet at $\delta = +6.5$ ppm, $J_{CF_2H} = 70.4$ Hz
$^{19}$F NMR:
  $\phi_{CF_2H} = -86.1$ ppm
  $\phi_{CHF} = -146.5$ ppm
  $\phi_{CF_3} = -84.5$ ppm
$^4J_{F-F(CF_2HOCHF)} = 5.8$ Hz
$J_{F-F(CF_2)} = 160.3$ Hz
$J_{F-H(CF_2H)} = 70.0$ Hz
$J_{F-H(CHF)} = 55.3$ Hz Mass Spectrum (electron impact): Format: m/e (intensity), fragment id.

$149(1)C_3H_2F_5O$, M—F; $101(17)C_2HF_4$; $69(9)CF_3$; $51(100)CF_2H$; $32(9)CHF$; $31(18)CF$

EXAMPLE 2

Isoflurane (15.5 g) was loaded into a 3-neck flask reactor equipped with a thermometer and stir bar. 2 ml of $BrF_3$ was added over 2½ hours while maintaining the temperature at about 14°–18° C. The reaction product was then allowed to stand overnight at ambient temperature The reaction product was treated with 5% sodium hydroxide and the resulting organic layer was separated (9.0 g) and then subjected to gas chromatography to obtain 8.0 g of the compound $CHF_2OCHFCF_3$ (62% yield).

EXAMPLE 3

A 200 ml Teflon reactor attached to a caustic scrubber was charged with 183.5 g (1.3 moles) of bromine trifluoride and the reactor lid attached. The bromine trifluoride charge was then stirred and 713.1 g (3.9 moles) of isoflurane added over a four hour period. The reactor temperature was maintained at 25°–30° C. by external cooling of the reactor with dry ice/carbon tetrachloride. The caustic scrubber (1.2 L of water, 304 g NaOH) was kept at $-10°$ to $-15°$ C. throughout the run. Following the addition of isoflurane, the reactor was allowed to stand at room temperature for one hour. Excess isoflurane was then distilled into the scrubber by heating the reactor to 55° C. The contents of the scrubber were then poured into a cold separatory funnel and the organic layer drained off and washed with cold water.

Gas chromatographic analyses were performed on a GOW-MAC Model HP5790 having a thermal conductivity detector (TCD) and HP 3392A integrator. The column was 1% SP1000 on 60/80 Carbopack B, 1/8' diameter X 20'. A flow rate of 60 cc/min, an injector temperature of 214° C., an oven temperature of 190° C. and a detector temperature of 214° C. was maintained All GC results were reported in area %.

GC analysis of the isolated material (565.2 g) showed it to be 98 0% $CHF_2OCHFCF_3$ ($t_r = 3.2$ minutes) and 1.6% isoflurane ($t_r = 6.13$ minutes). The percent conversion was thus 85% (87% yield). Some losses of the highly volatile product (b.p. 23.5° C.) occurred during the caustic work-up, which accounts for the less than quantitative results.

Attempts to moderate the reaction via the use of $CCl_4$ as a solvent produced no detectable amounts of $CHF_2OCHFCF_3$, but instead resulted in reaction with the solvent to produce chlorofluorocarbons (i.e., $CFCl_3$, $CF_2Cl_2$). The reaction of isoflurane with $BrF_3$ is likely ionic in nature, and the presence of elemental bromine was shown to have no effect on the reaction. Reaction of isoflurane with the less reactive interhalogen $IF_5$ produced only small amounts of product.

The following Table I summarizes the results of several experimental runs.

TABLE 1

REACTION OF ISOFLURANE WITH BROMINE TRIFLUORIDE

| Run No. | Reactants (molar ratio) | Temp (C.°) | Rxn time (hours) | $CH_2OCHFCF_3$ % Conversion | % Yield | Reaction Condition |
|---|---|---|---|---|---|---|
| 1 | Isoflurane:$BrF_3$ (1:1) | 25 | 2 | 0 | 0 | $CCl_4$ solvent |
| 2 | Isoflurane:$BrF_3$ (1:0.4) | 30 | 2 | 69 | 90 | Addition of $BrF_3$ to Isoflurane |
| 3 | Isoflurane:$BrF_3$ | 5–10 | 4 | 83 | 86 | Addition to |

TABLE 1-continued

| | REACTION OF ISOFLURANE WITH BROMINE TRIFLUORIDE | | | | | |
|---|---|---|---|---|---|---|
| Run No. | Reactants (molar ratio) | Temp (C.°) | Rxn time (hours) | $CH_2OCHFCF_3$ % Conversion | % Yield | Reaction Condition |
| | (1:1) | | | | | $BrF_3$ to Isoflurane |
| 4 | Isoflurane:$BrF_3$ (3:1) | 25-30 | 6 | 89 | 99 | Addition to Isoflurane to $BrF_3$ |
| 5 | Isoflurane:$BrF_3$ (3:1) | 25-30 | 3 | 85 | 87 | Addition to Isoflurane to $BrF_3$ |
| 6 | Isoflurane:$BrF_3$ (3:1) | 25-30 | 5 | 79 | 79 | Presence of $Br_2$; Addition of Isoflurane to $Br_3$ |

EXAMPLE 5

Test for Anesthetic Properties

Eight sPecific-pathogen-free, 2.5 month-old, male Sprague-Dawley rats weighing 381±18 g were housed individually in Plexiglass cylinders (chamber) having an internal diameter of 6.25 cm and a length of 29 cm. This diameter permitted the rat to crawl into the chamber, but prevented the rat from turning around.

The ends of the chamber were sealed with rubber stoppers. The stopper at the "head" end of the chamber was traversed by three catheters: one for sampling: one for injection of the compound $CHF_2OCHFCF_3$; and one for the delivery of oxygen. Oxygen was applied to the chamber at a bypass flow through rate of 500-600ml per minute. The head end of the chamber also contained a carbon dioxide adsorber, charged with 50 g to 55 g of fresh, commercial (Sodasorb) soda lime.

The stopper at the "tail" end of the chamber was traversed by a catheter, a hole for the tail, and a hole through which a small rectal temperature probe was passed. The catheter was used to flush oxygen through the tube prior to initiation of injection of the anesthetic composition and to draw off gas when oxygen was introduced to lower the concentration of the compound.

A rectal probe was placed and secured in each of the rats. The tail was led out through the hole in the stopper and sealed. After placement of the rat in the chamber, a 3-3.4 l/min. flow of oxygen was directed through the chamber for 15 minutes. The chamber then was sealed except for the opening at the head end of the chamber to the oxygen bypass.

A gaseous mixture of the composition was produced by adding 0.2-0.25 ml of the liquid compound $CHF_2OCHFCF_3$ to 20ml of oxygen in a 100 ml glass syringe sealed with a stopcock. This mixture was used to deliver the compound to the chamber. Anesthesia was rapidly induced by injection of a total of 50-75ml of this mixture.

Injection of the mixture of the compound and oxygen rapidly produced anesthesia. In general, the recovery was comparatively rapid. Each animal began to move within one to two minutes following evacuation of the chamber. All survived and appeared to be well 24 hours after anesthesia.

While there has been described what are at present considered to be preferred embodiments of the invention, it will be understood that various modifications may be made therein which are within the true spirit and scope of the invention.

We claim:

1. A method of producing the compound 2-(difluoromethoxy)-1,1,1,2-tetrafluoroethane comprising adding isoflurane to bromine trifluoride.

2. The method of claim 1, wherein the reaction resulting from said addition is at a temperature of 5° to 50° C.

3. The method of claim 2, wherein said reaction is at a temperature of about 30° C.

4. The method of claim 1, wherein the mole ratio of bromine trifluoride to isoflurane is about 0.3 to 1.

* * * * *

UNITED STATES PATENT AND TRADEMARK OFFICE
CERTIFICATE OF CORRECTION

PATENT NO. : 5,015,781
DATED : May 14, 1991
INVENTOR(S) : Robin et al.

It is certified that error appears in the above-identified patent and that said Letters Patent is hereby corrected as shown below:

Cover page, (21) Appln. No.: Delete 528,944 and insert in place thereof

-- 526,944 -- .

Signed and Sealed this

Fourteenth Day of June, 1994

Attest:

BRUCE LEHMAN

*Attesting Officer*  *Commissioner of Patents and Trademarks*